United States Patent [19]

Heller

[11] Patent Number: 5,200,116

[45] Date of Patent: * Apr. 6, 1993

[54] PHOTOCHROMIC CHROMENE COMPOUNDS

[75] Inventor: Harry G. Heller, Cardiff, Wales

[73] Assignee: PPG Industries, Inc., Pittsburgh, Pa.

[*] Notice: The portion of the term of this patent subsequent to Jun. 5, 2007 has been disclaimed.

[21] Appl. No.: 557,432

[22] Filed: Jul. 23, 1990

[51] Int. Cl.$^5$ .................... G02B 5/23; C07D 311/80; C07D 311/04; C07D 251/00
[52] U.S. Cl. .................................... 252/586; 252/589; 544/179; 544/180; 544/182; 544/238; 544/333; 544/336; 544/358; 546/196; 546/269; 546/339; 549/60; 549/389; 549/390; 549/391; 549/398; 549/399; 549/406; 549/408; 548/100; 548/146; 548/214
[58] Field of Search .................. 252/586, 589; 549/60, 549/389, 390, 391, 398, 399, 406, 408; 544/179, 180, 182, 238, 333, 336, 358; 546/196, 269, 339; 548/100, 146, 214

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 252/586 |
| 3,578,602 | 5/1971 | Ono et al. | 252/300 |
| 3,627,690 | 12/1971 | Casella | 252/586 |
| 3,973,966 | 8/1976 | Flannery et al. | 252/586 |
| 4,215,010 | 7/1980 | Hovey et al. | 252/300 |
| 4,238,501 | 12/1980 | Kabbe et al. | 424/283 |
| 4,342,668 | 8/1982 | Hovey et al. | 252/586 |
| 4,563,458 | 1/1986 | Widdig et al. | 514/253 |
| 4,637,698 | 1/1987 | Kwak et al. | 351/163 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,931,221 | 6/1990 | Heller | 252/586 |
| 4,946,880 | 8/1990 | Costanzi | 524/96 |
| 4,990,287 | 2/1991 | Bennion et al. | 252/586 |

FOREIGN PATENT DOCUMENTS 246114 11/1987 European Pat. Off. .
250193 12/1987 European Pat. Off. .
294056 12/1988 European Pat. Off. .

OTHER PUBLICATIONS

Padwa et al. J. Org. Chem. vol. 40, No. 8, 1975, 1142.

Primary Examiner—Robert L. Stoll
Assistant Examiner—Philip Tucker
Attorney, Agent, or Firm—Irwin M. Stein

[57] ABSTRACT

Described are a series of novel photochromic benzopyran and naphthopyran compounds substituted with (1) a cyclopropyl group and (2) a phenyl, substituted phenyl, or 5-member aromatic heterocyclic group at the 2-position of the benzopyran or naphthopyran ring. Also described are organic host materials that contain or that are coated with such compounds. Articles such as ophthalmic or plano lenses that incorporate the novel pyran compounds or combinations of the novel pyran compounds with other complementary photochromic compounds are described.

25 Claims, No Drawings

PHOTOCHROMIC CHROMENE COMPOUNDS

DESCRIPTION OF THE INVENTION

The present invention relates to novel benzopyran and naphthopyran compounds, especially novel photochromic benzopyran and naphthopyran compounds, and to compositions and articles containing such novel pyran compounds. Photochromism is a reversible phenomenon exhibited by a compound which, when exposed to light radiation involving ultraviolet rays, such as the ultraviolet radiation in sunlight or in the light of a mercury lamp, changes color and then returns to its original color if the ultraviolet radiation is discontinued or the compound is stored in the dark.

Photochromic compounds containing a pyran ring have been described heretofor. For Example, Becker U.S. Pat. No. 3,567,605 describes a series of pyran derivatives, including certain benzopyrans and naphthopyrans. These compounds are described as derivatives of chromene and are reported to undergo a color change, e.g., from colorless to yellow-orange on irradiation by ultraviolet light at temperatures below about minus 40° C. Irradiation of the compounds with visible light or upon raising the temperature to within the range of $-10°$ C. to 0° C. is reported to reverse the coloration to a colorless state.

European Patent Publication 246,114 describes a series of photochromic spiropyrans in which a spiroadamantane group is attached at the position adjacent to the oxygen in the pyran ring. U.S. Pat. No. 4,818,096 and European Patent Publication 250,193 describe photoreactive plastic lenses that are coated or impregnated with the photochromic spiropyrans of European Patent Publication 246,114 in combination with a blue photochromic benzopyran or naphthopyran having an aminophenyl substituent at the position adjacent to the oxygen in the pyran ring. European Patent Publication 294,056 describes a process for producing a polyurethane plastic having photochromic properties. Reversible cleavage photochromic compounds disclosed therein include a naphthopyran derivative in which the pyran ring is substituted at the position adjacent to the oxygen in the pyran ring with di(p-methoxyphenyl) substituents.

U.S. Pat. No. 4,931,221 describes chromenes containing two cyclopropyl groups at the position adjacent to the oxygen in the pyran ring. U.S. Pat. No. 4,563,458 describes certain 2H-chromenes as precursors of certain chroman-4-aldehydes, which are reacted with certain amines to prepare 4-aminomethylene-chromans and -chromenes that are used in medicaments.

Padwa et al in *J. Org. Chem.*, Volume 40, No. 8, 1975, page 1142, describes his investigation of the photochemical reactions of compounds of the type described in U.S. Pat. No. Becker 3,567,605, identifies the by-products and suggests pathways to the ring-opened color intermediates and the final non-colored phenolics. The color forms examined by the authors are reported as being unstable at room temperature. The authors do not suggest ways in which the stability of the examined compounds might be improved, nor any modification that might be made to the structure of the known pyran compounds.

It has now been discovered that novel photochromic chromenes substituted with (1) a cyclopropyl group and (2) a phenyl, substituted phenyl, or 5-member aromatic heterocyclic group at the 2-position of the benzopyran or naphthopyran ring may be prepared. Preferred are the aforedescribed naphthopyran compounds, especially the alpha naphthopyran compounds. The novel photochromic compounds of the present invention exhibit a reversible change from colorless to orange or orange-red in the activated form upon exposure to unfiltered sunlight compared to benzopyrans or naphthopyrans having alkyl groups attached at the 2-position of the pyran ring or a spirocycloalkyl group in the 2-position, such as the adamantylidene group, which are less orange or orange-red.

DETAILED DESCRIPTION OF THE INVENTION

In accordance with the present invention, there are provided novel benzopyran and naphthopyran compounds that may be graphically represented by the following graphic formulae I, II and III, wherein graphic formula I represents the 2-H-benzopyran series and graphic formulae II and III represent the isomeric naphthopyran series.

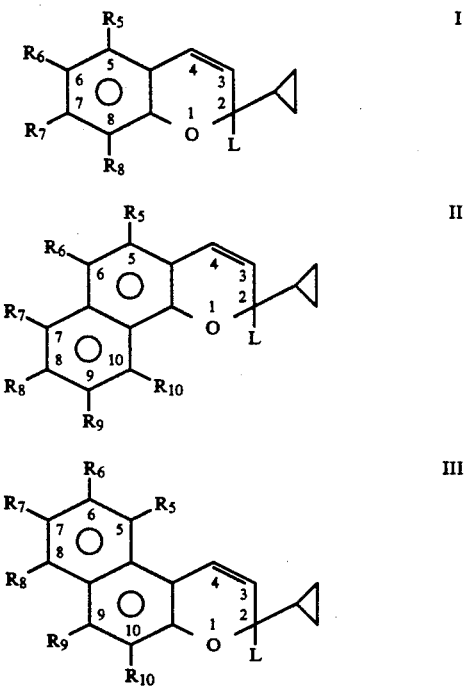

In the above graphic formulae I, II and III, and as used elsewhere in the description L may be selected from the group consisting of

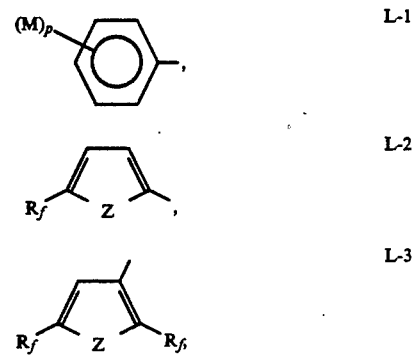

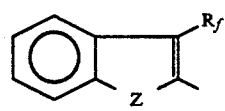

L-4

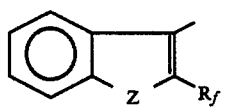

L-5 wherein Z is oxygen or sulfur, $R_f$ is selected from the group consisting of hydrogen, $C_1$–$C_4$ alkyl, phenyl($C_1$–$C_4$)alkyl and chloro, M is selected from the group consisting of $C_1$–$C_5$ alkyl, $C_1$–$C_5$ alkoxy, halogen, $C_1$–$C_4$ dialkylamino, or a heterocyclic nitrogen-containing substituent having 5 or 6 atoms in the ring, e.g., pyrrolidino, piperidino, morpholino, pyridino and 4-($C_1$–$C_4$ alkyl)piperazino, e.g., 4-methyl piperazino, and p is an integer of from 0 to 3, e.g., 1 or 2. When M is a heterocyclic nitrogen-containing substituent, p is usually 1. Accordingly, formula L-1 represents phenyl and substituted phenyl, L-2 represents 2-thienyl or 2-furyl (and substituted 2-thienyl or 2-furyl), L-3 represents 3-thienyl or 3-furyl (and substituted 3-thienyl or 3-furyl), and L-4 and L-5 represent benzannelated 2- and 3-thienyl or benzannelated 2- and 3-furyl, benzannelated substituted 2- and 3-thienyl or benzannelated substituted 2- and 3-furyl. In the case of L-1, the M substituent (when p is 1) is preferably at the ortho or para position. When M is a heterocyclic nitrogen-containing substituent, it is bonded to the phenyl group (L-1) via the ring nitrogen atoms.

Preferred embodiments include those wherein the chromenes of the present invention are represented by graphic formula II, L is phenyl or substituted phenyl (formula L-1), or a 5-membered aromatic heterocyclic group, such as described in formulae L-2, L-3, L-4 and L-5, $R_f$ is hydrogen, M is $C_1$–$C_3$ alkyl, $C_1$–$C_3$ alkoxy, fluoro, or chloro, and p is an integer of from 0 to 2, more preferably 1 or 2.

A variety of substituents may be placed on the benzo and naphtho portions of the benzopyran and naphthopyran rings. For example, such rings may be substituted in the positions represented respectively by $R_5$–$R_8$ in graphic formula I and $R_5$–$R_{10}$ in graphic formulae II and III with $C_1$–$C_{10}$ straight and branched chain alkyl, $C_5$–$C_7$ cycloalkyl, phenyl, mono- or disubstituted phenyl, $C_1$–$C_4$ alkoxy, halogen, or five-membered heteroaromatic groups connected to the benzopyran or naphthopyran ring by a single bond. More particularly, the benzo and naphtho portions of the benzopyran or naphthopyran rings may be substituted with $C_1$–$C_5$ alkyl, e.g., methyl, ethyl, n-propyl, isopropyl, butyl, and pentyl, $C_5$–$C_6$ cycloalkyl, e.g., cyclopentyl and cyclohexyl, $C_1$–$C_3$ alkoxy, e.g., methoxy, ethoxy and propoxy, chlorine (chloro), bromine (bromo), 2- or 3-furyl, 2- or 3-thienyl, phenyl, or ortho-, meta- or para-substituted phenyl, wherein the phenyl substituent is selected from the group consisting of $C_1$–$C_4$ alkyl, $C_1$–$C_4$ alkoxy, chloro and bromo. Preferably, when substituted the phenyl group is substituted with one substituent and that substituent is in the para position, e.g., p-methyl phenyl, p-chloro phenyl and p-methoxy phenyl. Still more particularly, the benzo or naphtho portion of the benzopyran or naphthopyran rings may be substituted with $C_1$–$C_3$ alkyl, $C_1$–$C_3$ alkoxy, chlorine (chloro), bromine (bromo), phenyl, or $C_1$–$C_3$ alkoxy phenyl, e.g., p-methoxy phenyl. When the benzopyran and naphthopyran rings are not substituted at positions represented by $R_5$–$R_8$ and $R_5$–$R_{10}$ respectively with one of the aforementioned substituent groups, $R_5$–$R_{10}$ are hydrogen. Typically, only one or two of the groups $R_5$–$R_8$ or $R_5$–$R_{10}$ is other than hydrogen.

In naming and referring to the benzopyran and naphthopyran compounds of graphic formulae I-III, positions on the rings are numbered counterclockwise starting with the oxygen atom as number (1). Such positions are indicated by the numbers appearing on the inside of the rings depicted in graphic formulae I-III. As shown in graphic formula I, the benzopyran ring may be substituted at the 5, 6, 7 and/or 8 positions, i.e., $R_5$, $R_6$, $R_7$ and/or $R_8$. In certain embodiments, the benzo portion of the benzopyran ring is substituted at the 5- position or the 5- and 8-positions, i.e., $R_5$, or $R_5$ and $R_8$. In such embodiments, $R_6$–$R_8$ or $R_6$ and $R_7$ are each hydrogen.

As shown in graphic formulae II and III, the naphtho portion of the naphthopyran ring may be substituted at the 5, 6, 7, 8, 9 and/or 10 position, i.e., $R_5$–$R_{10}$. In certain embodiments, the naphtho portion of the naphthopyran ring is substituted at the 5- position, at the 5- and 6-positions, or the 5- and 9-positions, i.e., $R_5$, $R_5$ and $R_6$, or $R_5$ and $R_9$. In such embodiments, $R_6$–$R_{10}$, $R_7$–$R_{10}$ or $R_6$–$R_8$ and $R_{10}$ are respectively each hydrogen.

Of particular current interest are the following benzopyrans and naphthopyrans:

(1) 2-cyclopropyl-2-p-methoxyphenyl-2H-naphtho[1,2-b]pyran.
(2) 2-cyclopropyl-2-p-methoxyphenyl-5-methyl-2H-naphtho[1,2-b]-pyran.
(3) 2-cyclopropyl-2,5'-dimethyl-3'-thienyl-2H-naphtho[1,2-b]-pyran.
(4) 2-cyclopropyl-2',5'-dimethyl-3'-furyl-2H-naphtho[1,2-b]-pyran.
(5) 2-cyclopropyl-2-phenyl-2H-naphtho[1,2-b]pyran.
(6) 2-cyclopropyl-2(2-thienyl)-2H-naphtho[1,2-b]pyran.
(7) 2-cyclopropyl-2(5-methyl-2-thienyl)-2H-naphtho[1,2-b]-pyran.
(8) 2-cyclopropyl-2(5-chloro-2-thienyl)-2H-naphtho[1,2-b]-pyran.

Introduction of the described groups at the 2-position of the naphthopyran ring causes a shift to longer wave lengths of the absorption band of their corresponding activated forms compared to 2-dialkyl substituted naphthopyrans, and tends to cause a color of orange to red with a higher conversion into the colored form, while providing a fast thermal fade at ambient temperatures, vis-a-vis, 2-dialkyl substituted naphthopyrans. Such properties make compounds of graphic formulae II–III useful in photochromic applications such as lenses for sun glasses, ski goggles, visors, camera lenses, windows, windshields, aircraft transparencies, plastic films and sheets, textiles and coating compositions containing organic photochromic compounds, such as paints. In general, the benzopyrans represented by graphic formula I exhibit color changes from colorless to from red to purple in unfiltered sunlight. The naphthopyrans represented by graphic formulae II and III generally exhibit color changes from colorless to from orange to red in unfiltered sunlight.

The benzopyrans and naphthopyrans described herein may be dissolved in common organic solvents such as benzene, toluene, chloroform, ethyl acetate, methyl ethyl ketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine and ethylene glycol. They may also be dispersed in liquids containing water and/or alcohols.

The aforedescribed pyran compounds may also be dissolved in colorless or transparent solutions prepared from transparent organic host materials, e.g., transparent polymers (or copolymers) or blends of such transparent polymers and optionally a suitable organic solvent, e.g., transparent polymers dissolved in one or more of the aforesaid described organic solvents. Examples of such solutions include a poly(vinyl acetate)-acetone solution, a nitrocellulose-acetonitrile solution, a poly(vinyl chloride)-methyl ethyl ketone solution, a poly(methylmethacrylate)- acetone solution, a cellulose acetate-dimethylformamide solution, a poly(vinyl pyrrolidone)-acetonitrile solution, a polystyrene-benzene solution and an ethyl cellulose-methylene chloride solution. The aforesaid photochromic solutions or compositions may be applied to a host material, e.g., a transparent substrate, such as cellulose triacetate, polyethylene terephthalate or baryta paper, and dried to obtain an article that will develop color on exposure to ultraviolet radiation and that will return to a colorless state by removing the source of ultraviolet radiation.

The pyran compounds described herein (or compositions containing them) may be applied to or incorporated within a coating composition applied to a suitable substrate; or applied to or incorporated within the article comprising the substrate, e.g., a polymerized organic material such as a synthetic polymeric plastic host material.

The benzopyrans and naphthopyrans described hereinabove may be incorporated in synthetic plastic materials customarily used for plastic lenses, both plano and ophthalmic, e.g., materials such as methyl methacrylate, polycarbonates and polymerizates prepared from OR ®-39 diallyl glycol carbonate monomer. See, for example, U.S. Pat. No. 2,542,386. Of the pyran compounds depicted in graphic formulae I–III, compounds represented by general formula II are currently preferred for synthetic plastic lenses. The term photochromic is used herein to describe the following stated desirable properties for photoreactive lenses; namely (a) a high quantum yield for coloring in the near ultraviolet; (b) a low quantum yield for bleaching with visible light; and (c) a fast thermal fade at ambient temperatures, but not so fast that the photochromic material does not color in unfiltered sunlight at ambient temperatures. In addition, the aforesaid properties are desirably retained in conventional rigid synthetic plastic materials customarily used for ophthalmic and plano lenses when such materials are treated to contain such pyran compounds.

On irradiation of the compounds of formula II with ultraviolet light, the naphthopyran ring opens reversibly at the carbon-oxygen bond between the number 2-carbon atom and the ring oxygen atom to form cis and trans structures. The formation of the open form of the compound is believed to be responsible for the coloring of the compounds on exposure to ultraviolet light. The photochromic compounds of graphic formulae I–III, particularly those of formulae II and III, will fade to the colorless state at normal ambient temperatures when not exposed to ultraviolet light.

The compounds of the present invention may be prepared by a process based on a Claisen rearrangement. In such process, the benzopyran and naphthopyran compounds described herein are prepared by heating the appropriate phenol or naphthol with the appropriate 1-cyclopropyl-1-L substituted propynol in an organic solvent and in the presence of a suitable acid catalyst under mild reaction conditions for a time sufficient to complete the reaction, i.e., usually between about 2 and about 6 hours. Organic solvents that may be used include xylene and toluene. Reaction temperatures will vary and typically range from about 100° C. to about 160° C. The particular reaction temperature will be a function of the boiling point of the chosen solvent. For example, when xylene is used as the solvent, reaction temperatures will generally be about 140° C., whereas if toluene is used as the solvent, reaction temperatures will typically be about 110° C. Examples of suitable acid catalysts include sulfuric acid, polyphosphoric acid, acidic alumina, chloroacetic acid or other acid catalysts. The reaction for the naphthopyran of graphic formula II wherein the L substituent is phenyl may be expressed by the following equation:

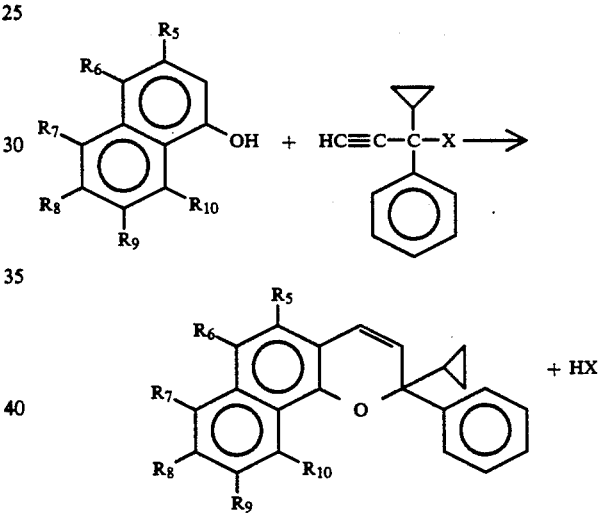

wherein $R_5$, $R_6$, $R_7$, $R_8$, $R_9$ and $R_{10}$ are the same as defined with respect to graphic formula II and X is hydroxyl, chloro, or acetoxy [$CH_3C(O)O$—]. In place of the naphthol depicted in the above equation, a corresponding phenol may be used to prepare benzopyrans of graphic formula I. The 1-cyclopropyl-1-L substituted propynol reactant may be prepared by reacting the appropriate L-group cyclopropyl ketone, with lithium acetylide, which is commercially available as an ethylene diamine complex, in a suitable organic solvent, such as tetrahydrofuran, dimethyl sulfoxide or toluene, followed by acidification with mineral acid.

Commercially available photoreactive inorganic glass lenses containing silver halide particles darken to a gray or brown color in sunlight. In order to match this color change in a plastic lens using the organic photochromic chromenes described in this application, such compounds may be mixed or used in conjunction with other appropriate organic photochromic materials to produce the commercially desired gray or brown color shade on exposure to ultraviolet light. For example, a compound which colors to yellow can be blended with a compound that colors to an appropriate purple to produce a brown shade. Similarly, a compound which is orange in its colored state will produce a shade of gray in conjunction with an appropriate blue coloring compound.

Many of the spiro(indolino) pyrido benzoxazine photochromic compounds described in U.S. Pat. No. 4,637,698 and spiro(indolino) naphthoxazines described in U.S. Pat. Nos. 3,562,172, 3,578,602, 4,215,010 and 4,342,668 color to purple or blue when activated, and these compounds may be used in admixture with or in conjunction with the orange/red photochromic chromene compounds described in this application to obtain a near gray or brown color when exposed to unfiltered sunlight. In addition, certain spiro(indolino) benzoxazines described in U.S. Pat. No. 4,816,584 color to shades of purple/blue when activated, and these compounds may be used in admixture with or in conjunction with the photochromic chromene compounds described in this application.

Spiro(indolino) pyrido benzoxazine (or naphthoxazine)-type compounds may be represented by the following graphic formula:

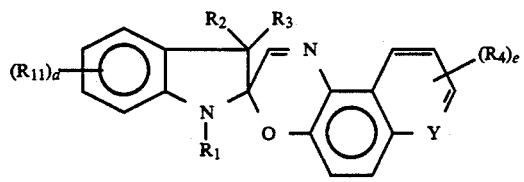

In the above graphic formula (1), $R_1$ is selected from the group consisting of $C_1$–$C_8$ alkyl, e.g., methyl, ethyl, propyl, butyl, etc., phenyl, phen($C_1$–$C_4$)alkyl, e.g., benzyl, naphth($C_1$–$C_4$)alkyl, e.g., 1-naphthylmethyl, allyl, acrylyl($C_2$–$C_6$)alkyl, methacrylyl($C_2$–$C_6$)-alkyl, carboxy($C_2$–$C_6$)alkyl, e.g., B-carboxyethyl, γ-carboxypropyl, δcarboxybutyl, cyano($C_2$–$C_6$)alkyl, e.g., β-cyanoethyl, γ-cyanopropyl, β-cyanoisopropyl, and δ-cyanobutyl, $C_1$–$C_4$ acyloxy($C_2$–$C_6$)alkyl, i.e., [$R_cC(O)OR_d$, wherein Rc is a $C_1$–$C_4$ alkyl and $R_d$ is a $C_2$–$C_6$ alkyl], e.g., acetoxyethyl, acetoxypropyl, propionyloxyethyl, acetoxybutyl, and propionyloxypropyl, hydroxy($C_2$–$C_6$)alkyl, e.g., hydroxyethyl, hydroxypropyl and hydroxybutyl, $(C_2H_4O)m\cdot CH_3$, wherein m is a number of from 1 to 6, and mono- and disubstituted phenyl, said phenyl substituents being selected from $C_1$–$C_4$ alkyl and $C_1$–$C_5$ alkoxy, e.g., methoxy ethoxy, propoxy, butoxy and pentoxy. Preferably, $R_1$ is selected from the group consisting of $C_1$–$C_4$ alkyl, phenyl, benzyl, 1-naphth($C_1$–$C_2$)-alkyl, such as 1-naphthylmethyl, carboxy($C_2$–$C_4$)alkyl, cyano($C_2$–$C_4$)alkyl, $C_1$–$C_4$ acyloxy($C_2$–$C_4$)alkyl, e.g., $C_1$–$C_4$ acyloxyethyl, hydroxy($C_2$–$C_4$)alkyl, e.g., $(C_2H_4O)m\cdot CH_3$, wherein m is a number of from 1 to 3, e.g., 2.

$R_2$ and $R_3$ of the above graphic formula (1) are each selected from the group consisting of $C_1$–$C_5$ alkyl, phenyl, mono- and disubstituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1$–$C_4$ alkyl and $C_1$–$C_5$ alkoxy radicals. More particularly, 2 and $R_3$ are each selected from $C_1$–$C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

Y in the graphic formula (1) may be carbon or nitrogen. The number and type of non-hydrogen substituent groups represented by $R_4$ will vary depending upon whether Y is carbon or nitrogen. Generally, when Y is carbon each $R_4$ substituent may be selected from the group consisting of halogen, e.g., chloro, fluoro, or bromo, $C_1$–$C_5$ alkyl, $C_1$–$C_5$ alkoxy, e.g., methoxy, ethoxy, propoxy, butoxy and pentoxy, nitro, cyano, thiocyano, $C_1$–$C_4$ monohaloalkyl, e.g., $C_1$–$C_4$ monochloroalkyl, such as chloromethyl and chloroethyl, $C_1$–$C_2$ polyhaloalkyl, as, for example, trihaloalkyl such as trichloroalkyl or trifluoroalkyl, e.g., trifluoromethyl and 2,2,2-trifluoroethyl, and monoalkylamino or dialkylamino wherein the alkyl moiety of the alkylamino group contains from one to four carbon atoms, e.g., methylamino, ethylamino, propylamino, dimethylamino and diethylamino.

The letter "e" in the graphic formula (1) is a number of from 0 to 1 or 2, e.g., 1, and denotes the number of non-hydrogen substituents. In particular, when "e" is 1 or 2 and Y is carbon, each $R_4$ substituent may be selected from the group $C_1$–$C_2$ alkyl, $C_1$–$C_2$ alkoxy, chloro, fluoro, bromo, nitro, and trifluormethyl. When "e" is 0 (zero), there are no $R_4$ substituents and all of the aromatic carbon atoms have their full complement of hydrogen atoms for the aromatic group shown.

When Y is nitrogen, each $R_4$ (non-hydrogen) substituent may be selected from $C_1$–$C_5$ alkyl, e.g., $C_1$–$C_2$ alkyl, $C_1$–$C_5$ alkoxy, e.g., $C_1$–$C_2$ alkoxy, and halogen, e.g., chloro, fluoro or bromo. Typically, "e" is 0 (zero) when Y is nitrogen and thus there are no $R_4$ substituents.

$R_{11}$ in the graphic formula (1) each may be selected from $C_1$–$C_5$ alkyl, halogen, $C_1$–$C_5$ alkoxy, nitro, cyano, $C_1$–$C_4$ monohaloalkyl, $C_1$–$C_4$ polyhaloalkyl, $C_1$–$C_8$ alkoxycarbonyl, and $C_1$–$C_4$ acyloxy, i.e., $R_cC(O)O—$, wherein $R_c$ is a $C_1$–$C_4$ alkyl, e.g., methyl. The letter "d" in graphic formula (1) may vary from 0 to 4, e.g., 0 to 2, such as 1 or 2, and denotes the number of non-hydrogen substituents. When "d" is 0 (zero), there are no $R_{11}$ substituents and all of the aromatic carbon atoms have the full complement of hydrogen atoms for the indole group.

More particularly, the spiro(indolino) pyridobenzoxazines may be represented by the following graphic formula:

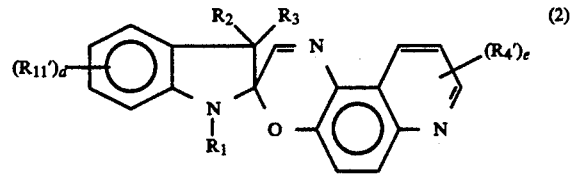

In graphic formula (2), $R_1$, $R_2$ and $R_3$ are the same as defined with respect to graphic formula (1). Each $R_4'$ may be selected from $C_1$–$C_5$ alkyl, e.g., $C_1$–$C_2$ alkyl, $C_1$–$C_5$ alkoxy, e.g., $C_1$–$C_2$ alkoxy and halogen, e.g., chloro, fluoro or bromo. The letter "e" may vary from 0 to 1. Commonly, "e" is 0, and thus, there are no $R_4'$ substituents. When "e" is 1, the $R_4'$ substituent may be located on any of the available carbon atoms of the pyridobenz moiety of the pyrido benzoxazine portion of the compound, i.e., at the 5', 6', 8' 9' or 10' positions, most usually at the 8', 9' or 10' positions. When "e" is 2, the $R_4'$ substituent may be the same or different and, in either case, are selected from the above-described group and are located at two of the aforedescribed available carbon atoms.

Each $R_{11}'$ in graphic formula (2) may be selected from the group consisting of $C_1$–$C_5$ alkyl, e.g., methyl, ethyl, propyl, butyl and pentyl, halogen, e.g., chloro and fluoro, $C_1$–$C_5$ alkoxy, e.g., methoxy, ethoxy, propoxy, butoxy and pentoxy, nitro, cyano, $C_1$–$C_4$ monohaloalkyl, e.g., chloromethyl, fluoromethyl, chloroethyl, chloropropyl, etc., $C_1$–$C_4$ polyhaloalkyl, e.g., trihaloalkyl, $C_1$–$C_8$ alkoxycarbonyl, and $C_1$–$C_4$ acyloxy, i.e., $R_cC(O)O$-, wherein $R_c$ is a $C_1$–$C_4$ alkyl, e.g., methyl. An example of an acyloxy group is acetoxy. While any halogen, i.e., chlorine, bromine, iodine and fluorine may be used in respect to the aforesaid halogen or haloalkyl substituents, chlorine, fluorine and bromine, particularly chlorine and fluorine are preferred for the halogen substituent and fluorine is preferred for the polyhaloalkyl substituent, e.g., trifluoromethyl, ($CF_3$). Preferably, $R_{11}'$ is selected from the group consisting of $C_1$–$C_2$ alkyl, chlorine, fluorine, $C_1$–$C_2$ trihaloalkyl, e.g., trihalomethyl such as trifluoromethyl and $C_1$–$C_5$ alkoxy.

The letter "d" in graphic formula (2) is a number from 0 to 4, e.g., 0 to 2, such as 1 or 2. When "d" is 2 or more, the $R_{11}'$ substituent may be the same or different and in either case, are selected from the aforedescribed group. The $R_{11}'$ substituent(s) may be located on any of the available carbon atoms of the indolino portion of the compound, i.e., at the 4, 5, 6 or 7 positions. When "d" is 2, the $R_{11}'$ substituents may be present at the 4 and 5, 5 and 6, 4 and 7 or 6 and 7 carbon atoms of the indolino moiety.

It is possible that the photochromic organic substances of graphic formula (2) (and 3) can be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole, or mixtures thereof. Thus, when "d" is 1, the photochromic substance may be substituted at the 4 position on the indoline ring, at the 6 position of that ring or comprise a mixture of such isomers. When "d" is 2, the photochromic substance may be substituted at any combination of the 4, 5, 6, or 7 carbon atoms of the indoline ring (as heretofore indicated) and may comprise an isomeric mixture of such compounds, e.g., a mixture of compounds having substituents at the 4 and 5, 4 and 6, 5 and 6, 4 and 7, 5 and 7, and 6 and 7 positions of the indoline ring. Commonly, when "d" is 2 the substituents are located at the 4 and 5, or 5 and 6 positions. Also contemplated are materials containing mixtures of such isomers, e.g., materials comprising 4 (and 6) and 5-substituted spiro(indolino) pyrido benzoxazines or naphthoxazines.

Non-limiting examples of spiro(indolino) pyridobenzoxazines selected from the description of graphic formula (2) that may be employed in the process of the present invention are described in Table 1. Such pyridobenzoxazines are those in which $R_1$, $R_2$, $R_3$, and $R_{11}'$ are as indicated in Table 1, the letter "e" is 0 (zero), and the letter "d" is 0, 1 or 2. A hyphen (—) indicates the absence of a non-hydrogen substituent.

TABLE 1

| Compound/ | $R_1$ | $R_2$ | $R_3$ | $R_{11}'$ | $R_{11}'$ |
|---|---|---|---|---|---|
| 1 | $CH_3$ | $CH_3$ | $CH_3$ | — | — |
| 2 | $CH_3$ | $CH_3$ | $CH_3$ | 4(6)-$CH_3$ | 5-$CH_3$ |

TABLE 1-continued

| Compound/ | $R_1$ | $R_2$ | $R_3$ | $R_{11}'$ | $R_{11}'$ |
|---|---|---|---|---|---|
| 3 | $CH_3$ | $CH_3$ | $CH_3$ | 5-$OCH_3$ | — |
| 4 | $CH_3$ | $CH_3$ | $CH_3$ | 5-Cl | 6-$CH_3$ |
| 5 | $CH_3$ | $CH_3$ | $C_2H_5$ | — | — |
| 6 | $CH_3$ | $CH_3$ | $C_2H_5$ | 5-$CH_3$ | (4)6-$CH_3$ |
| 7 | $CH_3$ | $C_2H_5$ | $C_2H_5$ | — | — |
| 8 | n-$C_4H_9$ | $CH_3$ | $C_2H_5$ | — | — |
| 9 | $CH_3$ | $CH_3$ | phenyl | — | — |
| 10 | $CH_3$ | phenyl | phenyl | — | — |
| 11 | $C_2H_5$ | $CH_3$ | $C_2H_5$ | 4(6)-$CH_3$ | 5-$CH_3$ |
| 12 | n-$C_4H_9$ | $CH_3$ | $C_2H_5$ | 5-$CH_3$ | (4)6-$CH_3$ |
| 13 | $CH_3$ | $CH_3$ | $CH_3$ | 5-$CH_3$ | (4)6-$CH_3$ |
| 14 | n-$C_3H_7$ | $CH_3$ | $CH_3$ | 5-$OCH_3$ | — |
| 15 | i-$C_3H_7$ | $CH_3$ | $CH_3$ | 5-$OCH_3$ | — |

Compound 2 in Table 1 may be named 1,3,3,4,(and 6),5-pentamethyl-spiro[indolino- 2,3' [3H]pyrido [3,2-f] [1,4] benzoxazine]. Similarly, compound 6 in Table 1 may be named 1,3,4(and 6),5-tetramethyl-3-ethyl-spiro[indolino-2,3' [3H] pyrido [3,2-f][1,4] benzoxazine]. Other compounds in Table 1 can be similarly named taking into account the different substituents. Moreover, compounds selected from the description of graphic formula (2) may be similarly named by substituting the substituents described with respect to $R_1$, $R_2$, $R_3$, $R_4'$ and $R_{11}'$ for those found in the description and in Table 1. When the letter "e" is 1 or more, the $R_4'$ substituent(s) are given a prime (') designation. Numbering of the pyrido benzoxazine portion of the molecule is counter clockwise starting with the nitrogen atoms of the oxazine ring as the number 1' position. Numbering of the indolino portion of the molecule is counter clockwise starting with the nitrogen atom as the number 1 position.

Spiro(indolino)naphthoxazines may be represented by the following graphic formula:

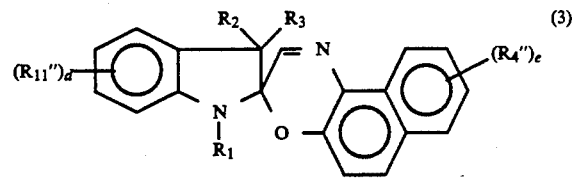

wherein $R_1$, $R_2$ and $R_3$ are the same as that described with respect to graphic formula (1).

$R_4''$ in graphic formula (3) each may be selected from the group consisting of halogen, e.g., chloro, fluoro, or bromo, $C_1$–$C_5$ alkyl, $C_1$–$C_5$ alkoxy (e.g., methoxy, ethoxy, propoxy, butoxy and pentoxy), nitro, cyano, thiocyano, $C_1$–$C_4$ monohaloalkyl, e.g., $C_1$–$C_4$ monochloroalkyl, such as chloromethyl and chloroethyl, $C_1$–$C_2$ polyhaloalkyl, as for example, trihaloalkyl, such as trichloroalkyl or trifluoroalkyl, e.g., trifluoromethyl and 2,2,2-trifluoroethyl, and monoalkylamino or dialkylamino, wherein the alkyl moiety of the alkylamino group contains from 1 to 4 carbon atoms, e.g., methylamino, ethylamino, propylamino, dimethylamino and diethylamino. More particularly, the $R_4''$ substituent may be selected from the group $C_1$–$C_2$ alkyl, $C_1$–$C_2$ alkoxy, chloro, fluoro, bromo, nitro and trifluormethyl, The letter "e" in graphic formula (3) is a number from 0 to 2, e.g., 1 or 2, and denotes the number of non-hydrogen $R_4''$ substituents. When "e" is 0, there are no $R_4''$ substituents and all of the aromatic carbon atoms of the naphtho moiety of the molecule represented by formula (3) have their full complement of hydrogen atoms for the naphtho group shown.

As in the case with graphic formula (Z), when "e" is 1, the $R_4''$ substituent may be located on any of the available carbon atoms of the naphtho moiety of the naphthoxazine portion of the molecule, i.e., at the 5', 6', 7' 8', 9' or 10' positions. Preferably, the $R_4''$ substituent is present on the 7', 8' or 9' carbon atoms. When "e" is 2, the $R_4''$ substituents may be same or different and in either case are selected from the above-described group. When "e" is 2, the $R_4''$ substituents are commonly located at the 7' and 9', or 8' and 10' positions. Numbering of the naphthoxazine portion of the molecule is done in the same manner as that described with regard to the pyrido benzoxazine portion of the molecule of formula (2). $R_{11}''$ and the letter "d" in graphic formula (3) may be the same as that described with respect to $R_{11}$ and "d" in graphic formula (1).

Non-limiting examples of spiro(indolino) naphthoxazines selected from the description of graphic formula (3) that may be used in the practice of the present invention are described in Table 2. Such spiro(indolino) naphthoxazines are those in which $R_1$, $R_2$, $R_3$, $R_4''$ and $R_{11}''$ are as indicated in Table 2, the letter "d" is 0, 1 or 2 and the letter "e" is 1. As in Table 1, a hyphen (—) indicates the absence of a non-hydrogen substituent. In Table 2, all of the $R_4''$ substituents are at the 9'-position.

TABLE 2

| Compound/ | $R_1$ | $R_2$ | $R_3$ | $R_4''$ (9'-) | $R_{11}''$ | $R_{11}''$ |
|---|---|---|---|---|---|---|
| 1 | $CH_3$ | $CH_3$ | $CH_3$ | $OCH_3$ | — | — |
| 2 | $CH_3$ | $CH_3$ | $CH_3$ | $OCH_3$ | 5-$CH_3$ | (4)6-$CH_3$ |
| 3 | $CH_3$ | $CH_3$ | $CH_3$ | $OCH_3$ | 5-$OCH_3$ | — |
| 4 | $CH_3$ | $CH_3$ | $CH_3$ | $OCH_3$ | 5-Cl | (4)6-$CH_3$ |
| 5 | $CH_3$ | $CH_3$ | $C_2H_5$ | $OCH_3$ | — | — |
| 6 | $CH_3$ | $CH_3$ | $C_2H_5$ | $OCH_3$ | 5-$CH_3$ | (4)6-$CH_3$ |
| 7 | $CH_3$ | $C_2H_5$ | $C_2H_5$ | $OCH_3$ | — | — |
| 8 | n-$C_4H_9$ | $CH_3$ | $C_2H_5$ | $OCH_3$ | — | — |
| 9 | $CH_3$ | $CH_3$ | phenyl | $OCH_3$ | — | — |
| 10 | $CH_3$ | phenyl | phenyl | $OCH_3$ | — | — |
| 11 | $CH_3$ | p-$C_6H_4OCH_3$ | p-$C_6H_4OCH_3$ | $OCH_3$ | — | — |
| 12 | $C_2H_5$ | $CH_3$ | $C_2H_5$ | $OCH_3$ | 5-$CH_3$ | — |
| 13 | n-$C_4H_9$ | $CH_3$ | $C_2H_5$ | $OCH_3$ | 5-$CH_3$ | — |

Compound 2 in Table 2 may be named 1,3,3,4(and 6),5-pentamethyl-9'methoxy- spiro [indolino-2,3' [3H]-naphth [2,1-b] [1,4]-oxazine]. Similarly, compound 6 in Table 2 may be named 1,3,4(and 6),5-tetramethyl-3-ethyl-9'-methoxyspiro [indolino-2,3' [3H]-naphth [2,1-b] [1,4]-oxazine. Other compounds in Table 2 can be similarly named taking into account the different substituents. Moreover, compounds selected from the description of graphic formula (3) may be similarly named.

Spiro(indolino) benzoxazines that may be used in combination with the chromene compounds of the present application may be represented by the following graphic formula:

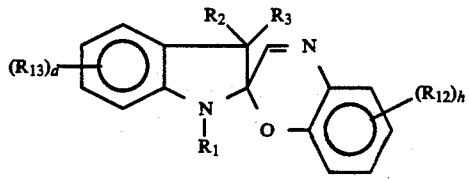

(4)

wherein $R_1$, $R_2$, $R_3$ and d are the same as defined with respect to graphic formula (1), $R_{13}$ and $R_{12}$ are each selected from the group $C_1$-$C_5$ alkoxy, preferably methoxy, and $C_1$-$C_5$ alkyl, and h is an integer of from 1 to 2.

Examples of contemplated compounds within the scope of graphic formula (4) are listed in Table 3. Compound 1 may be named: 7-methoxy-1',3',3',4'(and 6'), 5'-pentamethylspiro[2H-1,4-benzoxazine-2,2'-indoline]. Compounds 2–6 may be similarly named as substituted spiro(indolino) benzoxazines using the substituents described in Table I for such compounds. In naming the spiro(indolino) benzoxazines, the IUPAC rules of organic nomenclature have been used. The positions on the indolino portion of the molecule have been numbered counterclockwise starting with the nitrogen atom as the number one (1) position, and are identified by a prime number, e.g., 3'. The positions on the benzoxazine portion of the molecule have been numbered clockwise starting with the oxygen atom as the number one (1) position.

Generally, 5,7-dialkoxy, e.g., dimethoxy, substituted spiro(indolino) benzoxazines are magenta colored when activated. The 6,7-dialkoxy- and 7-alkoxy- substituted spiro(indolino) benzoxazines have a bluish coloration when activated.

TABLE 3

| Compound No. | $R_1$ | $R_2$ | $R_3$ | $R_{13}$ | $R_{13}$ | $R_{12}$ | $R_{12}$ |
|---|---|---|---|---|---|---|---|
| 1 | Me | Me | Me | 4(6)-Me | 5-Me | 7-OMe | — |
| 2 | Me | Me | Me | 4(6)-Me | 5-Me | 7-OMe | 5-OMe |
| 3 | Me | Me | Me | 5-OMe | — | 7-OMe | 5-OMe |
| 4 | Me | Me | Me | 4(6)-Me | 5-Me | 7-OMe | 6-OMe |
| 5 | Me | Me | Et | — | — | 7-OMe | 5-OMe |
| 6 | nBu | Me | Me | — | — | 7-OMe | 5-OMe |

Key:
Me = methyl
nBu = n-butyl
Et = ethyl
OMe = methoxy

The benzopyran or naphthopyran compounds of the present invention will usually be combined with or used in conjunction with the described spiro(indolino) pyrido benzoxazine, spiro(indolino) naphthoxazine, or spiro(indolino) benzoxazine compounds in amounts and in a ratio such that the organic host material containing the mixture of compounds exhibits a near grey or brown color when activated with unfiltered sunlight. The relative amounts of the oxazine and pyran compounds used will vary and depend in part upon the relative intensities of the color of the activated species of such compounds. Generally, the mole ratio of the spiro (indolino) oxazine compound to the pyran compound will vary from about 1:3 to about 3:1, e.g., between about 1:2 and about 2:1.

Photochromic compounds of the present invention, mixtures of such compounds with other photochromic compounds, or compositions containing same (hereinafter "photochromic substances") may be applied to or incorporated into a host material by known conventional methods. Such methods include dissolving or dispersing the substance within the host material, e.g., by imbibition of the photochromic substance into the host material by immersion or thermal transfer; incorporation of the photochromic substance as a separate layer between adjacent layers of the host material; and applying the photochromic substance as a coating to the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. See, for example, the disclosure of U.S. Pat. No. 4,816,584, column 9, line 67 through column 10, line 49, which describes various imbibition methods, and which disclosure is incorporated herein by reference.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances are unactivated.

Adjuvant materials may also be incorporated into the host material with the photochromic substances prior to or subsequent to their application or incorporation into the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers such as hindered amine light stabilizers and singlet oxygen quenchers, such as a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings or coatings that serve as oxygen barriers, e.g., a polyvinyl alcohol coating. Such coatings are known in the art.

Singlet oxygen quenchers that may be used as stabilizers include complexes of nickel (2+), i.e., $Ni^{2+}$, with an organic ligand, cobalt (III) tris-di-n-butyldithiocarbamate, cobalt (II) diisopropyldithiocarbamate, and nickel diisopropyldithiophosphate. Such singlet oxygen quenchers are used in stabilizing amounts.

Preferred are complexes of $Ni^{2+}$ such as [2,2'-Thiobis[4-(1,1,3,3-tetramethylbutyl)phenolato](butylamine)] nickel, which is sold under the tradename of CYASORB UV 1084; nickel [O-ethyl(3,5-di-tert-butyl-4-hydroxybenzyl)] phosphonate, which is sold under the tradename IRGASTAB 2002; nickel dibutyldithiocarbamate, which is sold under the tradename RYLEX NBC; bis[2,2'-thiobis-4-(1,1,3,3-tetramethylbutyl)phenolato] nickel, which is sold under the tradename UV-CHEK AM 101; nickel di-isopropyl dithiophosphate and other $Ni^{2+}$ complexes sold under the tradenames of UV-CHEK AM 105, UV-CHEK 126, and UV-CHEK AM 205.

Hindered amine light stabilizers that may be used include bis (2,2,6,6-tetramethyl-4-piperidinyl) sebacate, which is sold under the tradename TINUVIN 770; bis(1,2,2,6,6-pentamethyl-4-piperidinyl) sebacate, which is sold under the tradename TINUVIN 765; di(1,2,2,6,6-pentamethyl-4-piperidinyl)butyl-(3',5'-ditertiarybutyl-4-hydroxybenzyl)malonate, which is sold under the tradename TINUVIN 144; poly[(6-[(1,1,3,3-tetramethylbutyl)-amino]-1,3,5-triazine-2,4-diyl)-(6-[2,2,6,6-tetramethyl-4-piperidinyl]amino-hexamethylene)], which is sold under the tradename CHIMASSORB 944; and poly[[6-(morpholino)-s-triazine-2,4-diyl]][16-(2,2,6,6-tetramethyl-4-piperdyl)amino] hexamethylene], which is sold under the tradename CYASORB 3346. Other hindered amine light stabilizers that may be used are those sold under the tradename TINUVIN 622, SPINUVEX A-36 and HOSTAVIN TMN 20. Such stabilizers are used in stabilizing amounts.

The foregoing singlet oxygen quenchers and hindered amine light stabilizers may be used singly or in combination in amounts sufficient to enhance the light-fatigue resistance of the photochromic substance(s) described herein. Between 0.01 and about 5 percent by weight of the foregoing stabilizers may be used (alone or in combination) to improve the light fatigue resistance.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent material or an optically clear material, e.g., materials suitable for ophthalmic elements, such as ophthalmic lenses, or materials useful for applications such as windows, windshields, aircraft transparencies, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrenemethyl methacrylate) copoly(styrene-acrylonitrile), polyvinylbutyral and polymers, i.e., homocopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, which is sold under the trademark, LEXAN; a poly(methyl methacrylate), such as the material sold under the trademark, PLEXIGLAS; polymerizates of a polyol(allyl carbonate), especially diethylene glycol bis(allyl carbonate), which monomer is sold under the trademark CR-39, and copolymers of diethylene glycol bis(allyl carbonate) with other copolymerizable monomeric materials, e.g., copolymers with for example vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, cellulose acetate, cellulose propionate, cellulose butyrate, cellulose acetate butyrate, and polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by procedures well known in the art, e.g., U.S. Pat. Nos. 2,370,567 and 2,403,113.

The polyol (allyl carbonate) monomers may be represented by the graphic formula:

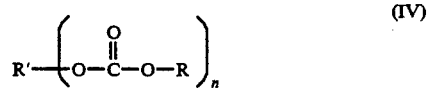

wherein R is the radical derived from an unsaturated alcohol and is commonly an allyl or substituted allyl group, R' is the radical derived from the polyol, and n is a whole number from 2–5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

wherein $R_0$ is hydrogen, halogen, or a $C_1$-$C_4$ alkyl group. Specific examples of R include the groups: allyl, 2-chloroallyl, 2-bromoallyl, 2-fluoroallyl, 2-methylallyl, 2-ethylallyl, 2-isopropylallyl, 2-n-propylallyl, and 2-n-butylallyl. Most commonly R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$-$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

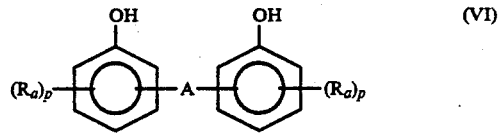

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), $R_a$ represents lower alkyl substituents of from 1 to 3 carbon atoms and halogen, e.g., chlorine and bromine, and p is 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH_2-CH_2-$, and $-CH_2CH_2CH_2-O-CH_2CH_2CH_2-$; alkylene polyether groups such as $-CH_2CH_2-O-CH_2CH_2-O-CH_2CH_2-$, and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2CH_2-O-CH_2CH_2-O-CO-O-CH_2CH_2-O-CH_2CH_2-$; and isopropylidene bis(para-phenyl), i.e., 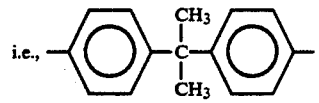

Most commonly, R' is $-CH_2CH_2-$, $-CH_2CH_2-O-CH_2CH_2-$, or $-CH_2CH_2-O-CH_2CH_2-O-CH_2CH_2-$.

Specific non-limiting examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which may be utilized in the invention herein contemplated are:

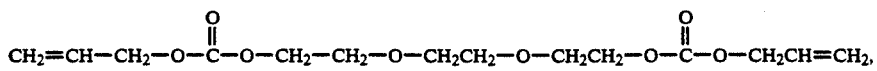

Triethylene Glycol bis(Allyl Carbonate)

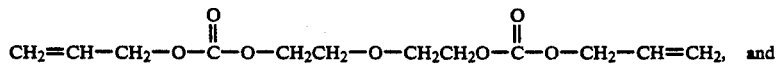

Diethylene Glycol bis(Allyl Carbonate)

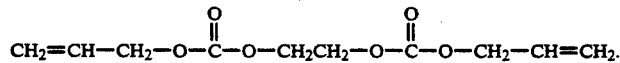

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alco- hol) and subsequent esterification by the allyl alcohol (or polyol), the monomer product can contain related monomer species in which the moiety connecting the allyl carbonate groups contains one or more carbonate groups. These related monomer species can be represented by the graphic formula:

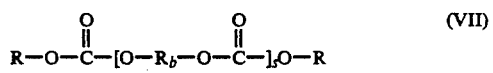 (VII)

wherein R is as defined above $R_b$ is a bivalent radical, e.g., alkylene or phenylene, derived from a diol, and s is a whole number from 2 to 5. The related monomer species of diethylene glycol bis(allyl carbonate) can be represented by the graphic formula,

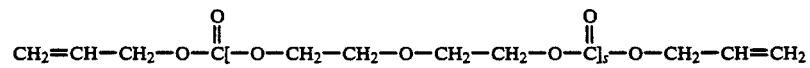 (VIII)

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer, i.e., prepolymer, can be used. In that embodiment, the monomer is thickened by heating or partially polymerized by using small, e.g., 0.5-1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

Polyfunctional acrylate monomers that may be used to prepare synthetic polymeric host materials are esterification products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

$$(CH_2=C(R_t)-C(O))-_nR''\qquad\qquad(IX)$$

wherein $R_t$ is hydrogen or methyl, n is the number 2, 3, or 4, and R'' is the multivalent radical, i.e., a bivalent, trivalent or quadravalent radical, remaining after removal of the hydroxy groups from a polyol, having from 2 to 4 hydroxy groups, e.g., a dibl, a triol or tetracarbinol respectively. More particularly, $R_t$ is hydrogen or methyl, and n is 2 or 3, more usually 2.

R'' may be selected from the group consisting of alpha, omega $C_2$-$C_8$ glycols, cyclohexane diol, diethylene glycol, triethylene glycol, tetraethylene glycol, dipropylene glycol, $C_2$-$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethyacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2=CH-$) grouping. Such compatible monomers include monofunctional acrylic and methacrylic acid esters, and vinyl esters of $C_2$-$C_6$ carboxylic acids, i.e., vinyl carboxylates. Preferably, the copolymerizable monomer is a non-aromatic, e.g., non-benzenoid, containing monomer. Monofunctional acrylic or methacrylic ester monomers may be graphically illustrated by the following formula, $$CH_2=C(R_t)-C(O)-O-R'''\qquad\qquad(X)$$

wherein $R_t$ is hydrogen or methyl, and $R'''$ is selected from the group consisting of $C_1$-$C_{12}$, e.g., $C_1$-$C_8$, alkyl, $C_5$-$C_6$ cycloalkyl, glycidyl and hydroxyethyl. Preferably, $R'''$ is a $C_1$-$C_4$ alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, l, dl)) and ethylene glycol. Examples of vinyl carboxylates include vinyl acetate, vinyl propionate, vinyl butyrate and vinyl valerate. In addition to and/or in place of the aforedescribed monofunctional copolymerizable monomer, monofunctional allylic and difunctional allylic copolymerizable compatible monomers may also replace a portion of the polyfunctional acrylate monomer. Monofunctional allylic monomers contemplated include allyl esters of $C_2$-$C_6$ carboxylic acids, $C_1$-$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula VI.

The amount of photochromic substance or composition-containing same applied to or incorporated into a host material is not critical provided that a sufficient amount is used to produce a photochromic effect discernible to the naked eye. Generally such amount can be described as a photochromic amount. The amount used depends often upon the intensity of color desired upon irradiation thereof and upon the method used to incorporate or apply the photochromic substances. Typically, the more compound applied or incorporated, the greater is the color intensity. Usually, the amount of each photochromic substance incorporated into or applied to the host material ranges from about 0.01 to about 20 percent by weight, more usually from about 0.05 to about 10 percent by weight, based on the weight of the host material. Stated another way, the amount of each photochromic substance used to impart a photochromic effect will typically vary from about 0.1 to about 10, e.g., 0.5 to 2 milligrams of the photochromic substance per square inch of the surface of the host material independent of the thickness of the host material article.

The present invention is more particularly described in the following examples which are intended as illustrative only, since numerous modifications and variations therein will be apparent to those skilled in the art.

EXAMPLE 1

Tin(IV) chloride (130.35 grams (g), 0.5 mole) in dichloromethane (150 cm$^3$) was added slowly with stirring over 30 minutes to a cooled solution of anisole (51.72 g, 0.478 moles) and cyclopropane carboxylic acid chloride (50 g, 0.478 mole) in dichloromethane (500 cm$^3$). When addition of the tin chloride was completed, the resulting mixture was stirred at room temperature for 2 hours, poured onto crushed ice (200 g) and stirred until the bright red color was discharged. The organic layer was dried with anhydrous magnesium sulfate, filtered and the dichloromethane solvent removed leaving a crude light brown oil product (86.84 g). The crude product was dissolved in toluene (300 cm$^3$) and the solution added to potassium t-butoxide (20 g, 0.178 mole) in a round bottom flask. The mixture was shaken (5 minutes) and then water (200 cm$^3$) was carefully added. The toluene layer was separated, dried and filtered. Toluene solvent was removed leaving p-methoxyphenyl cyclopropyl ketone (76.5 g). The ketone had a melting range of 175°-181° C. Despite the melting point range, an NMR spectrum of the product indicated that the ketone was of high purity. The foregoing procedures were repeated with similar results to obtain further amounts of the ketone.

Lithium acetylide/ethylene diamine complex (50 g, 0.543 mole) was added in small portions over 10 minutes to a dimethyl sulfoxide (250 cm$^3$) solution of p-methoxyphenyl cyclopropyl ketone (83.47 g, 0.473 mole). When the addition was complete, the mixture was stirred at room temperature overnight, poured onto crushed ice (300 g) and cold water (1 liter). The liberated oil was extracted into dichloromethane, dried and filtered. The dichloromethane solvent was removed leaving an oil (75.62 g), which was purified by column chromatography on silica gel (250 g) using a 1:9 mixture of ethyl acetate and petroleum (b.p. 60°-80° C.) as elutant. The product, 1-p-methoxyphenyl-1-cyclopropyl-propyn-1-ol, was obtained as a yellow oil (56.22 g).

A solution of 1-naphthol (21.39 g, 0.148 mole) and 1-p-methoxyphenyl-1-cyclopropylpropyn-1-ol (15 g, 0.074 mole) in toluene (200 cm$^3$) was boiled using a Dean and Stark apparatus to remove water. A solution of chloroacetic acid (0.35 g) in toluene (50 cm$^3$) was added gradually over a period of 3 hours to the boiling solution. The mixture was allowed to cool and then washed with 10% dilute sodium hydroxide to remove unreacted 1-naphthol and the chloroacetic acid catalyst. The mixture was then washed with water, dried, and filtered. The toluene solvent was removed leaving a brown oil which was chromatographed on silica gel (200 g) using a 1:9 mixture of ethyl acetate and petroleum (b.p. 60°-80° C.) as elutant. The photochromic fraction was separated and evaporated, leaving orange crystals which were crystallized twice from ethanol yielding the product 2-cyclopropyl-2-p-methoxyphenyl-2H-naphtho[1,2-b]pyran as pale yellow crystals. The product (10.32 g) had a melting point of 103°-104° C., and was obtained in 42% yield. When the photochromic product was incorporated into a test piece of a polymer prepared from diethylene glycol bis(allyl carbonate) and activated, it showed a colorless to intense orange color change.

EXAMPLE 2

A mixture of benzyl methyl ketone (134 g, 1 mole) and ethyl bromoacetate (168 g, 1 mole) was added to a mixture of mossy zinc (100 g) in toluene (500 cm$^3$) in a large flask. When the vigorous exothermic reaction had subsided, the mixture was boiled for 3 hours. The solution was cooled, and washed sequentially with dilute sulfuric acid, 10% aqueous sodium hydroxide and then with water. The organic layer was separated, dried and filtered. The toluene solvent was removed, leaving the hydroxy ester, ethyl 3-hydroxy-3-benzylbutanoate (152.8 g), as an orange oil. The ester's structure and purity were established by NMR spectroscopy.

The foregoing hydroxy ester (152 g, 0.76 mole) was dehydrated with phosphorus oxychloride (51.04 g, 0.37 mole) in pyridine (300 cm$^3$), which was added to the hydroxy ester dropwise over 15 minutes. When the addition was complete, phosphorus oxychloride and pyridine were removed under reduced pressure. Water (200 cm$^3$) was added to the dehydrated hydroxy ester and the mixture was extracted with ether. The ether extracts were washed first with dilute hydrochloric acid, then with water, and then dried and filtered. Ether solvent was removed leaving a mixture of the two unsaturated esters, i.e., ethyl 3-methyl-4-phenylbut-2- and 3-enoates as an oil (136 g).

The mixture of unsaturated esters (136 g, 0.666 mole) was boiled for 12 hours with 10% w/v ethanolic potassium hydroxide. Most of the ethanol was distilled off and the residual oil was dissolved in water and extracted carefully with toluene to remove neutral impurities. The aqueous solution was carefully acidified with 5M hydrochloric acid and the liberated oil extracted with ether. The ether extract was dried and filtered. Ether solvent was removed leaving a solid which was crystallized from ethanol giving colorless crystals of the mixed unsaturated acids 3-methyl-4-phenylbutenoic acids (111.8 g).

The mixture of unsaturated acids (111.8 g, 0.634 mole) was boiled for 4 hours with acetic anhydride (200 ml) and anhydrous sodium acetate (120 g). Acetic anhydride was removed under reduced pressure and the residue was extracted with ether. The ether extract was washed with 2M sodium carbonate solution and then with water, dried and filtered. The ether solvent was removed, leaving crude 1-acetoxy-3-methyl- naphthalene (84 g) as an oil.

Crude 1-acetoxy-3-methylnaphthalene (84 g, 0.42 mole) was boiled with 10% ethanolic potassium hydroxide (300 cm$^3$) for 3 hours. Ethanol was distilled off and the residue dissolved in water and extracted with toluene to remove neutral products. The aqueous alkaline solution was carefully acidified with dilute hydrochloric acid and the liberated 3-methyl-1-naphthol extracted with ether. The ether extract was washed with water, dried and filtered. Ether solvent was removed leaving 3-methyl-l-naphthol (18.4 g) as clear colorless crystals.

A solution of 3-methyl-1-naphthol (3.72 g, 0.024 mole) and 1-p-methoxyphenyl-1-cyclopropylpropyn-1-ol (9.51 g, 0.047 mole) in toluene (150 cm$^3$) was boiled using a Dean and Stark apparatus to remove water. A solution of chloroacetic acid (0.25 g) in toluene (50 cm$^3$) was added gradually over a period of 2 hours to the boiling solution. After boiling for a further hour, the mixture was allowed to cool and then washed with 10% dilute sodium hydroxide to remove unreacted 3-methyl-1-naphthol and the chloroacetic acid catalyst. The mixture was then washed with water, dried, and filtered. The toluene solvent was removed leaving a brown oil which was chromatographed on silica gel (100 g) using a 1:9 mixture of ethyl acetate and petroleum (b.p. 60°-80° C.) as elutant. The photochromic fraction was separated and evaporated, leaving a solid which was crystallized twice from ethanol yielding the product 2-cyclopropyl-2-p-methoxyphenyl-5-methyl-2H-naphtho[1,2-b] pyran as pale yellow crystals.

The product was obtained at 26% yield. When the photochromic product was incorporated into a test piece of a polymer prepared from diethylene glycol bis(allyl carbonate) and activated, it showed a colorless to intense orange color change.

EXAMPLE 3

2,5-Dimethylfuran (50 g, 0.520 mole) and cyclopropylcarbonyl chloride (54.36 g, 0.520 mole) were dissolved in dichloromethane (500 ml) and cooled in an ice bath. Tin(IV) chloride (143.28 g, 0.550 mole) in dichloromethane (150 ml) was added slowly over 1 hour to the cooled solution with stirring to form a very dark brown solution. The mixture was warmed to room temperature and stirred for a further hour. The mixture was then poured into cold water (750 ml) and stirred rapidly for 30 minutes. The dichloromethane layer was washed with water (2×200 ml) and dried over magnesium sulfate. The dichloromethane solvent was removed to yield the crude ketone 2,5-dimethyl-3-furyl cyclopropyl ketone as a dark brown oil (70.3 g).

Lithium acetylide/ethylene diamine complex (33.15 g, 0.36 mole) was added with rapid stirring to a dimethyl sulfoxide (250 ml) solution of 2,5-dimethyl-3-furyl cyclopropyl ketone (56 g, 0.341 mole) at room temperature. The mixture was stirred for 48 hours and poured into cold water (1 liter). The liberated brown oil was extracted into dichloromethane and dried. The dichloromethane solvent was removed leaving the acetylenic alcohol, 1-(2,5-dimethyl-3-furyl)-1-cyclopropylpropyn-1-ol, as a dark brown oil, which was filtered through silica gel (150 g) to give an orange/brown oil (28 g).

A solution of 1-naphthol (15.16 g, 0.11 mole) and 1-(2,5-dimethyl-3-furyl)-1-cyclopropylpropyn-1-ol (10 g, 0.053 mole) in toluene (150 cm$^3$) was boiled using a Dean and Stark apparatus to remove water. A solution of chloroacetic acid (0.20 g) in toluene (30 cm$^3$) was added gradually over a period of 3 hours to the boiling solution. After boiling for a further hour, the mixture was allowed to cool and then washed with 10% dilute sodium hydroxide to remove unreacted 1-naphthol and the chloroacetic acid catalyst. The mixture was then washed with water, dried, and filtered. The toluene solvent was removed leaving a brown oil which was chromatographed on silica gel (100 g) using a 1:9 mixture of ethyl acetate and petroleum (b.p. 60°-80° C.) as elutant. The photochromic fraction was separated and evaporated, leaving an oil (2.73 g). The NMR spectrum of the oil was consistent with the required product, 2-cyclopropyl-2-(2,5-dimethyl-3-furyl)-2H-naphtho[1,2-b]pyran.

When the photochromic product was incorporated into a test piece of a polymer prepared from diethylene glycol bis(allyl carbonate) and activated, it showed a colorless to orange color change.

EXAMPLE 4

2,5 Dimethylthiophene (50 g, 0.446 mole) and cyclopropylcarbonyl chloride (54.36 g, 0.52 mole) were dissolved in dichloromethane (500 ml) and cooled in an ice bath. Tin(IV) chloride (122.44 g, 0.470 mole) in dichloromethane (150 ml) was added slowly over 1 hour with stirring to form a deep red solution. The mixture was warmed to room temperature and stirred for a further hour. The mixture was then poured into cold water (750 ml) and stirred rapidly for 30 min. The dichloromethane layer was washed with cold water and dried over magnesium sulfate. The dichloromethane solvent was removed to give the ketone, 2,5-dimethyl-3-thienyl cyclopropyl ketone, as a brown oil (73.25 g).

Lithium acetylide/ethylene diamine complex (34.99 g, 0.38 mole) was added to a dimethylsulfoxide (250 ml) solution of 2,5-dimethyl-3-thienyl cyclopropyl ketone (65 g, 0.361 mole) at room temperature with rapid mechanical stirring The mixture was stirred for 48 hours and poured into cold water (1 liter). The liberated brown oil was extracted into dichloromethane (2×200 ml), dried and the dichloromethane solvent removed leaving a dark brown oil, which was filtered through silica gel (150 g) to give the acetylenic alcohol, 1-(2,5-dimethyl-3-thienyl)-1-cyclopropylpropyn-1-ol, as a red-brown oil (38.36 g).

A solution of 1-naphthol (21.58 g, 0.015 mole) and 1-(2,5-dimethyl-3-thienyl)-1-cyclopropylpropyr:-1-ol (15.44 g, 0.075 mole) in toluene (200 cm$^3$) was boiled using a Dean and Stark apparatus to remove water. A solution of chloroacetic acid (0.5 g) in toluene (50 cm$^3$) was added gradually over a period of 3 hours to the boiling solution. After boiling for a further hour, the mixture was allowed to cool and then washed with 10% dilute sodium hydroxide to remove unreacted 1-naphthol and the chloroacetic acid catalyst. The mixture was then washed with water, dried, and filtered. The toluene solvent was removed leaving a brown oil which was chromatographed on silica gel (100 g) using a 1:9 mixture of ethyl acetate and petroleum (b.p. 60°–80° C.) as elutant. The photochromic fraction was separated and evaporated, leaving an oil (7.16 g). The NMR spectrum of the oil was consistent with the required product, 2-cyclopropyl-2-(2,5-dimethyl-3-thienyl)-2H naphtho[1,2-b]pyran.

When the photochromic product was incorporated into a test piece of a polymer prepared from diethylene glycol bis(allyl carbonate) and activated, it showed a colorless to orange color change.

EXAMPLE 5

A solution of 1-naphthol (33.49 g, 0.232 mole) and 1-phenyl-1-cyclopropylpropy::-1-ol (20 g, 0.116 mole) in toluene (250 ml) was boiled using a Dean and Stark apparatus to remove water. A solution of chloroacetic acid (0.5 g) in toluene (50 ml) was added gradually over a period of 5 hours to the boiling solution. The mixture was allowed to cool and was washed with 10% dilute sodium hydroxide to remove unreacted 1-naphthol and the chloroacetic acid catalyst. The washed mixture was then washed with water, dried and the toluene solvent removed leaving a brown oil (20.86 g) which was chromatographed on silica gel (200 g) using a 1:9 mixture of ethyl acetate and petroleum (b.p. 60°–80° C.) as elutant. The photochromic fraction was isolated as a yellow oil, which solidified on tituration in petroleum to give the product, 2-cyclopropyl-2-phenyl-2H- naphthol[1,2-b]pyran, as a colorless powder (4.65 g) which, in toluene solution, showed a photochromic change from colorless to orange when activated.

EXAMPLE 6

Lithium acetylide/ethylene diamine complex (15.65 g, 0.17 mole) was added to a dimethyl sulfoxide (100 ml) solution of 2-thienyl cyclopropyl ketone (25 g, 0.164 mole) at room temperature with rapid mechanical stirring. The mixture was stirred overnight and poured into cold water (500 ml). The liberated oil was extracted into ether, dried and the ether solvent removed to yield a yellow/orange oil (14.66 g), which was purified by chromatography on silica gel (200 g) using 9:1 petroleum (b.p. 60°–80° C.) and ethyl acetate as elutant to give the acetylenic alcohol, 1-(2-thienyl)-1-cyclopropylpropyn-1-ol, as a light yellow oil (10.71 g) after removal of solvent.

A solution of 1-naphthol (12.94 g, 0.09 mole) and the acetylenic alcohol, 1-(2-thienyl)-1-cyclopropylpropyn-1-ol (8 g, 0.45 mole) in toluene (100 ml) was boiled using a Dean and Stark apparatus to remove water. A solution of chloroacetic acid (0.2 g) in toluene (30 ml) was added slowly over 3 hours to the boiling solution. The mixture was allowed to cool and was washed with 10% dilute sodium hydroxide solution to remove unreacted 1-naphthol and chloroacetic acid catalyst. The washed mixture was then further washed with water, dried and the toluene solvent removed leaving a brown oil (9.31 g), which was chromatographed twice on silica gel (100 g) using a mixture of 1:9 ethyl acetate and petroleum (b.p. 60°–80° C.) as elutant. The photochromic fraction was isolated as a red oil (4.32 g), which was titurated in petroleum (b.p. 60°–80° C.) to form the naphthopyran product 2-cyclopropyl-2-(2-thienyl) 2H-naphthol[1,2-b] pyran, as light yellow crystals (3.13 g) which, in toluene solution, showed a photochromic change from colorless to orange when activated.

EXAMPLE 7

Tin(VI) chloride (208.4 g, 0.8 mole) in dichloromethane (7200 cm$^3$) was added slowly, with stirring over 3 hours to a cooled solution of 2-methylthiophene (75 g, 0.764 mole) and cyclopropane carboxylic acid chloride (81.5 g, 0.78 mole) in dichloromethane (500 cm$^3$). When the addition was complete, the mixture was stirred at room temperature for 2 hours, poured onto crushed ice (200 g) and stirred until a bright red color was discharged. The organic layer was dried (anhydrous magnesium sulfate), filtered and the dichloromethane solvent removed leaving a crude light brown oil product (99 g). An NMR spectrum of the product indicated that it was predominantly the required ketone.

Lithium acetylide/ethylene diamine complex (50 g, 0.543 mole) was added in small portions over 10 minutes to a dimethyl sulfoxide (250 cm$^3$) solution of the crude light brown oil (90.27 g). When the addition was complete, the mixture was stirred at room temperature overnight, poured onto crushed ice (300 g) and cold water (1 liter). The liberated oil was extracted into dichloromethane, dried and filtered. The dichloromethane solvent was removed leaving an oil which was purified by column chromatography on silica gel (250 g) using a 1:9 mixture of ethyl acetate and petroleum (b.p. 50°–80° C.) as elutant. The product, 1-(5-methyl-2-thienyl)-1-cyclopropylpropyn-1-ol, was obtained as a yellow oil (46 g).

A solution of 1-naphthol (62.24 g, 0.432 mole) and 1-(5-methyl-2-thienyl)-1-cyclopropylpropyn-1-ol (41.5 g, 0.216 mole) in toluene (200 cm$^3$) was boiled using a Dean and Stark apparatus to remove water. A solution of chloroacetic acid (1 g) in toluene (50 cm$^3$) was added gradually over a period of 3 hours to the boiling solution. The mixture was allowed to cool and then washed with a 10% aqueous sodium hydroxide solution to remove unreacted 1-naphthol and the chloroacetic acid catalyst. The mixture was then washed with water, dried, and filtered. The toluene solvent was removed leaving a brown oil which was chromatographed on silica gel (200 g) using a 1:9 mixture of ethyl acetate and petroleum (b.p. 60°–80° C.) as elutant. The photochromic fraction was separated and evaporated, leaving orange crystals which were crystallized twice from ethanol yielding the product 2-cyclopropyl-2-(5-methyl-2-thienyl)-2H-naphtho[1,2-b]pyran as pale yellow crystals (10 g). When the photochromic product was incorporated into a test piece of a polymer prepared from diethylene glycol bis(allyl carbonate) and activated, it showed a colorless to orange color change.

EXAMPLE 8

Tin(IV) chloride (101.6 g, 0.89 mole) in dichloromethane (150 cm$^3$) was added slowly, with stirring over 30 minutes to a cooled solution of 2-chlorothiophene (41.50 g, 0.350 mole) and cyclopropane carboxylic acid chloride (38.15 g, 3.65 mole) in dichloromethane (500 cm$^3$). When the addition was complete, the mixture was stirred at room temperature for 2 hours, poured onto crushed ice (ZOO g) and stirred until a bright red color was discharged. The organic layer was dried over anhydrous magnesium sulfate, filtered and the dichloromethane solvent removed leaving a crude light brown oil product (6Z.63 g). An NMR spectrum of the product indicated that it was predominantly the desired ketone.

Lithium acetylide/ethylene diamine complex (Z7.62 g, 0.300 mole) was added in small portions over 10 minutes to a dimethyl sulfoxide (250 cm$^3$) solution of the foregoing ketone (50 g, 0.268 mole). When the addition was complete, the mixture was stirred at room temperature overnight, poured onto crushed ice (300 g) and cold water (1 liter). The liberated oil was extracted into dichloromethane, dried and filtered. The dichloromethane solvent was removed leaving an oil which was purified by column chromatography on silica gel (250 g) using a 1:9 mixture of ethyl acetate and petroleum (b.p. 60°–80° C.) as elutant. The product, 1-(5-chloro-2-thienyl)-1-cyclopropylpropyn-1-ol, was obtained as a yellow oil (66 g).

A solution of 1-naphthol (27.12 g, 0.188 mole) and 1-(5-chloro-2-thienyl)-1-cyclopropylpropyn-1-ol (20 g, 0.0S mole) in toluene (200 cm$^3$) was boiled using a Dean and Stark apparatus to remove water. A solution of chloroacetic acid (0.5 g) in toluene (50 cm$^3$) was added gradually over a period of 3 hours to the boiling solution. The mixture was allowed to cool and then washed with 10% aqueous sodium hydroxide solution to remove unreacted 1-naphthol and the chloroacetic acid catalyst. The mixture was then washed with water, dried, and filtered. The toluene solvent was removed leaving a brown oil which was chromatographed on silica gel (200 g) using a 1:9 mixture of ethyl acetate and petroleum (b.p. 60°–80° C.) as elutant. The photochromic fraction was separated and evaporated, leaving orange crystals which were crystallized twice from ethanol yielding the product 2-cyclopropyl-2-(5-chloro-2-thienyl)-2H-naphtho[1,2-b]pyran as pale yellow crystals (4.7 g). When the photochromic product was incorporated into a test piece of a polymer prepared from diethylene glycol bis(allyl carbonate) and activated, it showed a colorless to orange color change.

Although the present invention has been described with reference to specific details of certain embodiments thereof, it is not intended that such details should be regarded as limitations upon the scope of the invention except as and to the extent that they are included in the accompanying claims.

What is claimed is

1. A compound represented by the following graphic formulae:

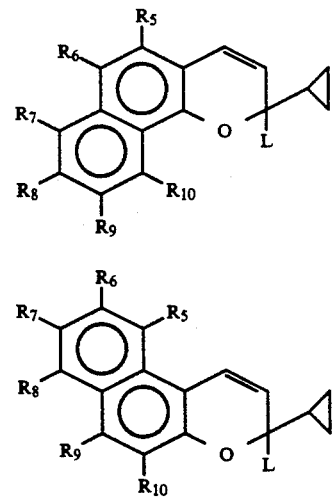

wherein L is selected from the groups represented by

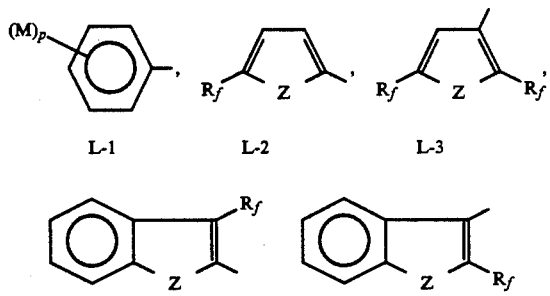

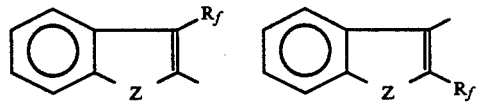

Z is oxygen or sulfur, $R_f$ is selected from the group consisting of hydrogen, $C_1$–$C_4$ alkyl, phenyl ($C_1$–$C_4$) alkyl, and chloro. M is selected from the group consisting of $C_1$–$C_5$ alkyl, $C_1$–$C_5$ alkoxy, halogen, $C_1$–$C_4$ dialkylamino, and a heterocyclic nitrogen-containing substituent having 5 or 6 atoms in the heterocyclic ring; p is an integer of from 0 to 3; and $R_5$–$R_{10}$ are each selected from the group consisting of $C_1$–$C_{10}$ alkyl, $C_5$–$C_7$ cycloalkyl, phenyl, mono- or disubstituted phenyl, $C_1$–$C_4$ alkoxy, halogen, and five-membered heteroaromatic groups, said phenyl substituent(s) being selected from the group consisting of $C_1$–$C_4$ alkyl, $C_1$–$C_4$ alkoxy, chloro and bromo.

2. A compound according to claim 1 wherein p is 1 when M is a heterocyclic nitrogen-containing substituent.

3. A compound according to claim 1 wherein $R_f$ is hydrogen; M is selected form the group consisting of $C_1$–$C_3$ alkyl, $C_1$–$C_3$ alkoxy, fluoro and chloro; p is an integer of from 0 to 2, $R_5$ and $R_{10}$ are each selected from the group consisting of $C_1$–$C_5$ alkyl, $C_5$–$C_6$ cycloalkyl, $C_1$–$C_3$ alkoxy, chloro, bromo, 2- or 3-furyl, 2- or 3-thienyl, phenyl or mono-substituted phenyl.

4. A compound according to claim 3 wherein p is 1 or 2, $R_5$–$R_{10}$ are each selected from the group consisting of $C_1$–$C_3$ alkyl, $C_1$–$C_3$ alkoxy, chloro, bromo, phenyl or $C_1$–$C_3$ alkoxy phenyl.

5. A naphthopyran compound according to claim 3 represented by the graphic formula,

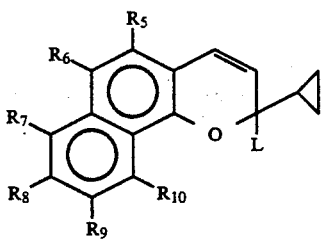

6. A naphthopyran compound according to claim 4 represented by the graphic formula,

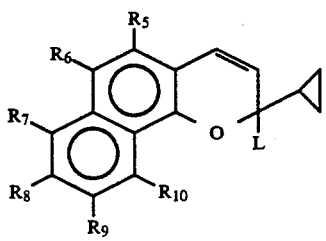

7. A naphthopyran compound according to claim 5 wherein the number of the substituents $R_5$–$R_{10}$ that are other than hydrogen is 1 or 2.

8. A naphthopyran compound according to claim 6 wherein the number of the substituents $R_5$–$R_{10}$ that are other than hydrogen is 1 or 2.

9. A photochromic article comprising a solid transparent organic host material and a photochromic amount of a photochromic compound represented by one of the following graphic formulae:

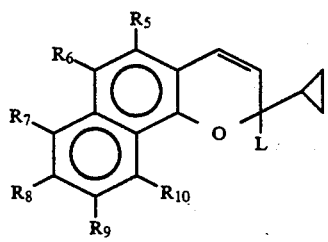

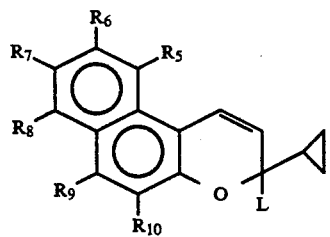

wherein L is selected from the groups represented by

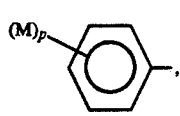 , 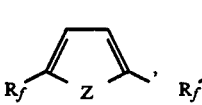 , 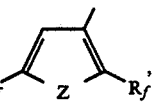

L-1   L-2   L-3

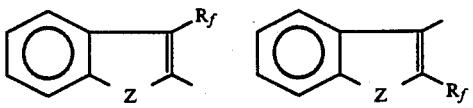

Z is oxygen or sulfur, $R_f$ is selected from the group consisting of hydrogen, $C_1$–$C_4$ alkyl, phenyl ($C_1$–$C_4$) alkyl, and chloro. M is selected from the group consisting of $C_1$–$C_5$ alkyl, $C_1$–$C_5$ alkoxy, halogen, $C_1$–$C_4$ dialkylamino, and a heterocyclic nitrogen-containing substituent having 5 or 6 atoms in the heterocyclic ring; p is an integer of from 0 to 3; and $R_5$–$R_{10}$ are each selected from the group consisting of $C_1$–$C_{10}$ alkyl, $C_5$–$C_7$ cycloalkyl, phenyl, mono- or disubstituted phenyl, $C_1$–$C_4$ alkoxy, halogen, and five-membered heteroaromatic groups, said phenyl substituent(s) being selected from the group consisting of $C_1$–$C_4$ alkyl, $C_1$–$C_4$ alkoxy, chloro and bromo.

10. A photochromic article according to claim 9 wherein $R_f$ is hydrogen; M is selected form the group consisting of $C_1$–$C_3$ alkyl, $C_1$–$C_3$ alkoxy, fluoro and chloro; p is an integer of from 0 to 2, $R_5$ and $R_{10}$ are each selected from the group consisting of $C_1$–$C_5$ alkyl, $C_5$–$C_6$ cycloalkyl, $C_1$–$C_3$ alkoxy, chloro, bromo, 2- or 3-furyl, 2- or 3-thienyl, phenyl or mono-substituted phenyl.

11. A photochromic article according to claim 10 wherein the organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

12. The photochromic article of claim 11 wherein the transparent polymerized organic host material is a homopolymer or copolymer of diethylene glycol bis(allyl carbonate).

13. The photochromic article of claim 12 wherein the photochromic compound is present in an amount of from 0.01 to 20 weight percent.

14. The photochromic article of claim 13 wherein the article is an optical element.

15. The photochromic article of claim 14 wherein the optical element is a lens.

16. A photochromic article comprising a solid transparent organic host material containing a photochromic amount of each of (a) photochromic substance selected from the group consisting of spiro(indolino) naphthoxazines, spiro(indolino) pyrido benzoxazines, and spiro(indolino) benzoxazines that, when activated, color to shades of purple and/or blue, and (b) photochromic substance represented by one of the following graphic formulae:

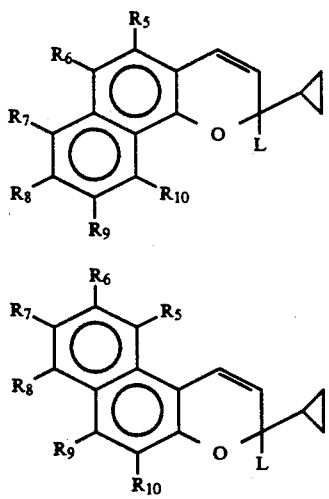

wherein L is selected from the groups represented by

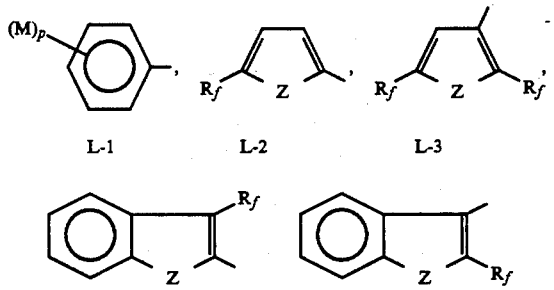

Z is oxygen or sulfur, $R_f$ is selected from the group consisting of hydrogen, $C_1$-$C_4$ alkyl, phenyl ($C_1$-$C_4$) alkyl, and chloro. M is selected from the group consisting of $C_1$-$C_5$ alkyl, $C_1$-$C_5$ alkoxy, halogen, $C_1$-$C_4$ dialkylamino, and a heterocyclic nitrogen-containing substituent having 5 or 6 atoms in the heterocyclic ring; p is an integer of from 0 to 3; and $R_5$-$R_{10}$ are each selected from the group consisting of $C_1$-$C_{10}$ alkyl, $C_5$-$C_7$ cycloalkyl, phenyl, mono- or disubstituted phenyl, $C_1$-$C_4$ alkoxy, halogen, and five-membered heteroaromatic groups, said phenyl substituent(s) being selected from the group consisting of $C_1$-$C_4$ alkyl, $C_1$-$C_4$ alkoxy, chloro and bromo.

17. The photochromic article of claim 16 wherein $R_f$ is hydrogen, M is selected form the group consisting of $C_1$-$C_3$ alkyl, $C_1$-$C_3$ alkoxy, fluoro and chloro; p is an integer of from 0 to 2, $R_5$ and $R_{10}$ are each selected from the group consisting of $C_1$-$C_5$ alkyl, $C_5$-$C_6$ cycloalkyl, $C_1$-$C_3$ alkoxy, chloro, bromo, 2- or 3-furyl, 2- or 3-thienyl, phenyl or mono-substituted phenyl.

18. The photochromic article of claim 16 wherein the transparent host material is selected from the group consisting of polymers of polyol(allyl carbonate) monomer, polyacrylates, poly(alkylacrylates), polymers of polyfuntional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

19. The photochromic article of claim 18 wherein the host material is prepared from homopolymers and copolymers of diethylene glycol bis(allyl carbonate).

20. The photochromic article of claim 19 wherein the photochromic compounds are each present in amounts of from about 0.05 to about 10 weight percent.

21. The photochromic article of claim 20 wherein the photochromic article is an optical element.

22. The photochromic article of claim 20 wherein the ratio of the spiro(indolino) oxazine substance to the pyran substance varies from about 1:3 to about 3:1.

23. The photochromic article of claim 22 wherein the photochromic article is an ophthalmic lens.

24. The photochromic article of claim 22 wherein a stabilizing amount of stabilizer selected from the group consisting of hindered amine light stabilizer, singlet oxygen quencher and mixtures of such stabilizers are present with said photochromic substance in said article, thereby to enhance the light-fatigue resistance of the photochromic substance.

25. The photochromic article of claim 24 wherein the amount of stabilizer used is between 0.01 and about 5 percent by weight.

* * * * *